(12) United States Patent
Hendrikse

(10) Patent No.: US 9,048,077 B2
(45) Date of Patent: Jun. 2, 2015

(54) SYSTEMS, DEVICES, AND METHODS FOR SAMPLE ANALYSIS USING MASS SPECTROMETRY

(71) Applicant: Smiths Detection Montreal Inc., Montreal Quebec (CA)

(72) Inventor: Jan Hendrikse, Whitby Ontario (CA)

(73) Assignee: SMITHS DETECTION MONTREAL INC., Montreal (CA)

( * ) Notice: Subject to any disclaimer, the term of this patent is extended or adjusted under 35 U.S.C. 154(b) by 0 days.

(21) Appl. No.: 14/362,555

(22) PCT Filed: Dec. 5, 2012

(86) PCT No.: PCT/IB2012/002917
§ 371 (c)(1),
(2) Date: Jun. 3, 2014

(87) PCT Pub. No.: WO2013/084069
PCT Pub. Date: Jun. 13, 2013

(65) Prior Publication Data
US 2014/0339417 A1 Nov. 20, 2014

Related U.S. Application Data

(60) Provisional application No. 61/566,932, filed on Dec. 5, 2011.

(51) Int. Cl.
*H01J 49/04* (2006.01)
*H01J 49/26* (2006.01)
*B01D 59/44* (2006.01)
*H01J 49/00* (2006.01)

(52) U.S. Cl.
CPC ............. *H01J 49/04* (2013.01); *H01J 49/0031* (2013.01); *H01J 49/0036* (2013.01); *H01J 49/0081* (2013.01)

(58) Field of Classification Search
CPC .... H01J 49/0422; H01J 49/0495; H01J 49/24
USPC .................... 250/282, 281, 288, 292, 441.11; 73/863.12
See application file for complete search history.

(56) References Cited

U.S. PATENT DOCUMENTS

| 6,894,276 B1 | 5/2005 | Yasuaki et al. |
| 2002/0014586 A1 | 2/2002 | Clemmer |
| 2007/0158543 A1 | 7/2007 | Clowers et al. |

(Continued)

OTHER PUBLICATIONS

Supplementary European Search Report for EP 12856205, mailed Apr. 1, 2015, 7 pages.

*Primary Examiner* — Nikita Wells
(74) *Attorney, Agent, or Firm* — Casimir Jones S.C.

(57) ABSTRACT

A mass spectrometry system for screening a sample for one or more analytes includes a pre-mass spectrometry screening apparatus configured to pre-screen an ionized sample to generate output correlated to the composition of the sample, and a mass spectrometer. A sample gate is opened to allow flow of at least a portion of the ionized sample to the mass spectrometer and closed to prevent flow of the ionized sample to the mass spectrometer. A processing system compares results of the pre-mass spectrometry screening to an analyte database, wherein correlation of the results to an analyte within the analyte database comprises a preliminary positive identification. When the processing system determines that a preliminary positive identification is made, it causes the gate to open for a period of time. However, when the processing system determines that a preliminary positive identification is not made, it causes the gate to remain closed.

21 Claims, 4 Drawing Sheets

(56) References Cited

U.S. PATENT DOCUMENTS

2008/0121797 A1    5/2008   Wu et al.
2011/0253891 A1* 10/2011 Hashimoto et al. ........... 250/288
2014/0033835 A1*   2/2014   Hendrikse et al. ......... 73/863.12

\* cited by examiner

SYSTEMS, DEVICES, AND METHODS FOR SAMPLE ANALYSIS USING MASS SPECTROMETRY

BACKGROUND

Trace detection technologies are used to screen for the presence of minute amounts of substances. Trace detection systems are typically employed in security settings to detect the presence of explosives, narcotics, or other contraband. Trace detection technologies make use of minute amounts of vapors and other particles given off by substances of interest and/or materials used in their manufacture, transpiration, or concealment.

Mass spectrometry, for example ion trap mass spectrometry, has been identified as having potential utility in trace detection. Mass spectrometry measures the mass-to-charge ratio of charged particles from a sample to determine the masses of the particles, and thus the elemental composition of the sample. During mass spectrometry the components of the sample are ionized, which results in the formation of charged particles (ions). The ions are separated according to their mass-to-charge ratio in an analyzer by electromagnetic fields, and detected to produce an ion signal. The ion signal may then be processed into mass spectra for analysis.

SUMMARY

Techniques are described for screening a sample for the presence or absence of one or more analytes using mass spectrometry, in particular, ion trap mass spectrometry, and so forth. In one or more embodiments, the techniques may be implemented using a mass spectrometry system. The mass spectrometry system includes a pre-mass spectrometry screening apparatus configured to generate ions from the sample to create an ionized sample and to pre-screen the ionized sample to generate output correlated to the composition of the sample, and a mass spectrometer configured to receive at least a portion of the ionized sample and generate a mass spectrum of the sample. The mass spectrometry system further includes a sample gate. The sample gate is configured to be opened to allow flow of at least a portion of the ionized sample from the pre-mass spectrometry apparatus to the mass spectrometer, and to be closed to prevent flow of the ionized sample from the pre-mass spectrometry screening apparatus to the mass spectrometer. A processing system compares results of the pre-mass spectrometry screening to an analyte database, wherein correlation of the results of the pre-mass spectrometry screening to an analyte within the analyte database comprises a preliminary positive identification. When the processing system determines that a preliminary positive identification is made, the processing system causes the sample gate to open for a period of time. However, when the processing system determines that a preliminary positive identification is not made, the processing system causes the sample gate to remain closed.

In one or more embodiments, the techniques may be implemented as a method of screening a sample for one or more analytes by mass spectrometry. In accordance with the method, ions are generated from the sample to create an ionized sample. A pre-mass spectrometry screening of the ionized sample is then performed. A processing system compares results of the pre-mass spectrometry screening to an analyte database stored in a memory, wherein correlation of the result of the pre-mass spectrometry screening to an analyte within the database comprises a preliminary positive identification. When the processing system determines that a preliminary positive identification is made, a sample gate is opened for a period of time to allow a portion of the ionized sample to pass through to an ion trap of a mass spectrometer. When the processing system determines that a preliminary positive identification is not made, the sample gate is caused to remain closed to prevent the ionized sample from passing through to the ion trap of the mass spectrometer.

This Summary is provided to introduce a selection of concepts in a simplified from that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description is described with reference to the accompanying figures. In the figures, the left-most digit(s) of a reference number identify the figure in which the reference number first appears. The use of the same reference number in different instances in the description and the figures may indicate similar or identical items.

DETAILED DESCRIPTION

Overview

Mass spectrometry is most selective when ions with a specific mass are selected, fragmented, and the mass spectrum of the fragment is analyzed (e.g., using MS/MS techniques). However, performing a full MS/MS analysis on all samples collected is prohibitively time consuming, and thus is not well suited for use in security screening in a real-world environment. Moreover, repeated analysis of samples by mass spectrometry results in rapid contamination of the ion trap of the mass spectrometer. Consequently, the frequency with which maintenance must be performed on the ion trap is generally too high.

Accordingly, systems and methods are described for sample pre-analysis prior to mass spectrometry analysis. In an implementation, a system for performing a pre-separation or analysis step may use Ion Mobility Spectroscopy (IMS) to pre-screen an initial analysis and guide and/or manage subsequent MS/MS analysis. A pre-analysis improves efficiency because the flow and analysis of ions in an analytical instrument (e.g., mass spectrometer) is time consuming, and too much ion flow may influence the analysis accuracy. Information obtained from the pre-separation step is used to control a gating mechanism that permits or disallows flow of ions for further analysis.

Example Implementations

Figure 1:
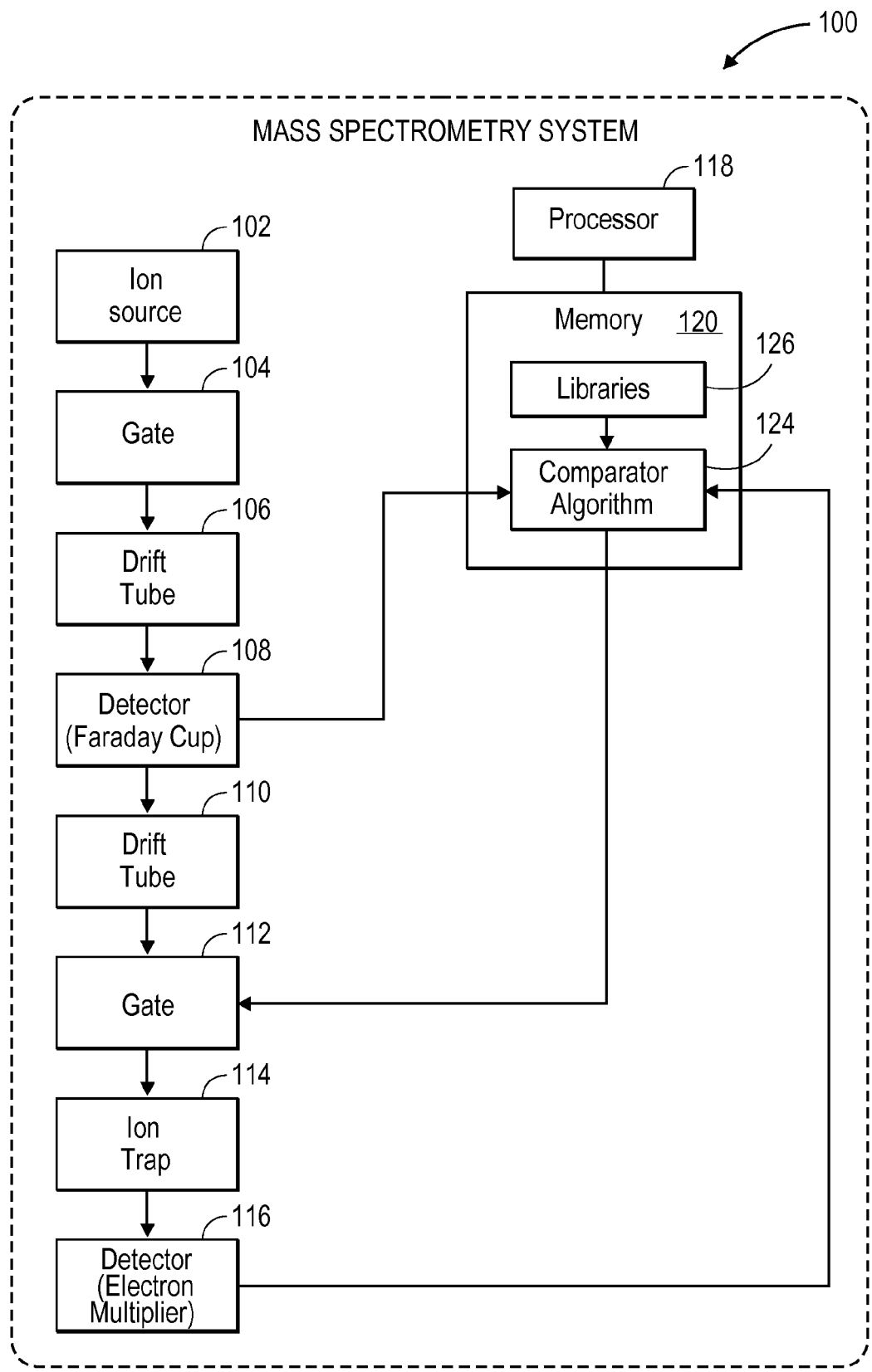
FIG. 1 is a diagrammatic illustration of sample analysis systems in accordance with example implementations of the present disclosure.

FIG. 1 illustrates a mass spectroscopy system 100 in accordance with example implementations of the present disclosure. As shown, the mass spectroscopy system 100 includes an ion source 102, a sample gate 104, 112 configured to block flow of sample from the pre-MS-screening apparatus, wherein the sample gate is configured to allow a portion of the sample to pass through upon correlation of output from the pre-MS-screening apparatus to one or more analytes in a library 126, a drift tube 106, 110 for separating ions with different mobilities in time, a detector 108, 116 that detects ion concentration, a second drift tube 110 for delaying the ion package while an IMS identification is made, an ion trap 114, a library 126 (e.g., an analyte database) of spectra, a processing system (e.g., processor 118) configured (e.g., via software) to allow rapid comparison of generated spectra and the library spectra, and a comparator algorithm 124 configured to compare a generated spectra with a library spectra (e.g., embodied in software run by said processor) and determines to open or close the second sample gate 112 based on the spectra comparison. The mass spectroscopy system 100 may include a pre-mass spectrometry screening apparatus such as an ion mobility spectroscope, a gas chromatograph, a differential IMS, a travelling wave IMS, and a high field Asymmetric waveform IMS. The pre-mass spectrometry screening apparatus may include the ion source 102, sample gate 104, a drift tube 106, and detector 108 and may be configured to generate output correlated to the composition of a sample.

The mass spectroscopy system 100 includes an ion source 102. An ion source 102 may include a device that is configured to create charged particles and convert gas phase sample molecules into ions. In some implementations, an ion source 102 may include a device configured to utilize atmospheric-pressure chemical ionization to create the ions and charged particles. In atmospheric-pressure chemical ionization, sample material is heated to yield a vapor that is swept into a small drift chamber where a beta radiation source ionizes the molecules. The resulting ions—separated according to size, mass and geometry—accelerate towards a detector 108, such as a Faraday cup. In some implementations, the molecules of the sample may be ionized by a device configured to utilize corona discharge, electrospray ionization (ESI), atmospheric pressure photoionization (APPI), and/or a radioactive source. As used herein, the term "sample" is used in its broadest sense, referring to the material analyzed, or to be analyzed. Samples may be natural and/or synthetic, biological or environmental, and may contain any number and any combination of analytes, materials, compounds, compositions, particles, etc. (e.g., explosive materials, narcotics, contraband, etc.).

In some instances, the ion source 102 can ionize material from a sample of interest in multiple steps. For example, the ion source 102 may generate a corona that ionizes gases that are subsequently used to ionize the sample. Example gases include, but are not necessarily limited to: nitrogen, water vapor, gases included in air, and so forth.

In implementations, the ion source 102 can operate in positive mode, negative mode, switch between positive and negative mode, and so forth. For example, in positive mode the ion source 102 can generate positive ions from a sample of interest, while in negative mode the ion source 102 can generate negative ions. Operation of the ion source 102 in positive mode, negative mode, or switching between positive and negative mode can depend on implementation preferences, a predicted sample type (e.g., explosive, narcotic, toxic industrial chemicals), and so forth. Further, the ion source 102 can be pulsed periodically (e.g., based upon sample introduction, gate opening, the occurrence of an event, and so on).

The mass spectroscopy system 100 includes a sample gate 104, 112, 112. The sample gate 104, 112 may be configured to be briefly opened or closed to allow flow of a sample or a portion of a sample to flow through a drift region (e.g., the first drift tube 106, the second drift tube 110) and to a detector (e.g., a Faraday Cup, electron multiplier 116). In implementations, the sample gate 104, 112 may include a fast switching gas valve configured to block ions as well as neutral gas molecules. This may be especially advantageous if a vacuum within the mass spectrometer is maintained by a pumping system with a limited capacity. In another implementation, the sample gate 104, 112 may include a fast pneumatic valve. In some implementations, the sample gate 104, 112 may include a mesh of wires to which an electrical potential difference is applied or removed. In yet other implementations, the sample gate 104, 112 may include an electronic shutter. For example, the sample gate 104, 112 may include a Bradbury-Nielsen shutter. In some embodiments, the sample gate 104, 112 comprises an ion gate.

The mass spectroscopy system 100 includes a drift tube 106, 110 for separating ions with different mobilities in time. In the drift tube, chemical species separate based on the ion mobility. The drift tube 106, 110 has electrodes (e.g., focusing rings formed by one or more conductor traces) spaced along its length for applying an electric field to draw ions along the drift tube 106, 110 and/or to direct the ions toward a detector disposed generally opposite the sample gate 104, 112 in the drift tube 106, 110. For example, the drift tube 106, 110, including the electrodes, can apply a substantially uniform field in the drift tube 106, 110. The sample ions can be collected at a detector 108 or electron multiplier 116, which can be connected to analysis instrumentation for analyzing the flight times of the various sample ions. For instance, a detector 108 or electron multiplier 116 at the far end of the drift tube 106, 110 can collect ions that pass along the drift tube 106, 110. Ions are recorded at the detector 108 or electron multiplier 116 in order from the fastest to the slowest, generating a response signal characteristic for the chemical composition of the measured sample.

In implementations, a drift gas can be supplied through the drift tube 106, 110 in a direction generally opposite the ions' path of travel to the detector 108 or electron multiplier 116. For example, the drift gas can flow from adjacent the detector 108 or electron multiplier 116 toward the sample gate 104, 112. Example drift gases include, but are not necessarily limited to: nitrogen, helium, air, air that is re-circulated (e.g., air that is cleaned and/or dried) and so forth. For example, a pump can be used to circulate air along the drift tube 106, 110 against the direction of flow of ions. The air can be dried and cleaned using, for instance, a molecular sieve pack.

The mass spectroscopy system 100 includes a detector 108 configured to detect ions based on their charge. In some implementations, the detector 108 may include a simple Faraday plate or cup. A Faraday cup is a metal (conductive) cup designed to catch charged particles in a vacuum. The resulting current may be measured and analyzed to determine the number of ions or electrons hitting the cup. In other implementations, the detector 108, 116 may include an electron multiplier. An electron multiplier may include a vacuum-tube structure that multiplies incident charges. In a process called secondary electron emission, a single electron can, when bombarded on secondary emissive material, induce emission of roughly 1 to 3 electrons. If an electric potential is applied between this metal plate and yet another, the emitted electrons will accelerate to the next metal plate and induce secondary emission of still more electrons. This can be repeated multiple times resulting in a large shower of electrons all collected by a metal anode. The electrons may be measured and correlated to an analyte database.

The mass spectroscopy system 100 includes a processor 118, a library 126, and a comparator algorithm 124. In implementations, a mass spectroscopy system 100, including some or all of its components, can operate under computer control. For example, a processor 118 can be included with or in a mass spectroscopy system 100 to control the components and functions of mass spectroscopy system 100 described herein using software, firmware, hardware (e.g., fixed logic circuitry), manual processing, or a combination thereof The terms "controller" "functionality," "service," and "logic" as used herein generally represent software, firmware, hardware, or a combination of software, firmware, or hardware in conjunction with controlling the mass spectroscopy system 100. In the case of a software implementation, the module, functionality, or logic represents program code that performs specified tasks when executed on a processor (e.g., CPU or CPUs). The program code may be stored in one or more computer-readable memory devices (e.g., comparator algorithm 124, library 126, internal memory and/or one or more tangible media), and so on. The structures, functions, approaches, and techniques described herein can be implemented on a variety of commercial computing platforms having a variety of processors.

For example, detector 108, 116 may be coupled with the processor 118 for controlling the energy supplied to the ion source 102. The processor 118 may include a processing system, a communications module, and a memory. The processing system provides processing functionality for the processor 118 and may include any number of processors, microcontrollers, or other processing systems, and resident or external memory for storing data and other information accessed or generated by the controller. The processing system may execute one or more software programs, which implement techniques described herein. The processing system is not limited by the materials from which it is formed or the processing mechanisms employed therein, and as such, may be implemented via semiconductor(s) and/or transistors (e.g., using electronic integrated circuit (IC) components), and so forth. The communications module is operatively configured to communicate with components of the detector 108, 116. The communications module is also communicatively coupled with the processing system (e.g., for communicating inputs from the detector 108, 116 to the processing system). The communications module and/or the processing system can also be configured to communicate with a variety of different networks, including, but not necessarily limited to: the Internet, a cellular telephone network, a local area network (LAN), a wide area network (WAN), a wireless network, a public telephone network, an intranet, and so on.

The memory is an example of tangible computer-readable media that provides storage functionality to store various data associated with operation of the controller, such as software programs and/or code segments, or other data to instruct the processing system and possibly other components of the controller to perform the steps described herein. Thus, the memory can store data, such as a program of instructions for operating the mass spectroscopy system 100 (including its components), spectral data, and so on. Although a single memory is shown, a wide variety of types and combinations of memory (e.g., tangible memory, non-transitory) may be employed. The memory may be integral with the processing system, may include stand-alone memory, or may be a combination of both.

The memory may include, but is not necessarily limited to: removable and non-removable memory components, such as Random Access Memory (RAM), Read-Only Memory (ROM), Flash memory (e.g., a Secure Digital (SD) memory card, a mini-SD memory card, and/or a micro-SD memory card), magnetic memory, optical memory, Universal Serial Bus (USB) memory devices, hard disk memory, external memory, and other types of computer-readable storage media. In implementations, the memory may include removable Integrated Circuit Card (ICC) memory, such as memory provided by a Subscriber Identity Module (SIM) card, a Universal Subscriber Identity Module (USIM) card, a Universal Integrated Circuit Card (UICC), and so on.

In some embodiments, the systems, devices, and methods comprise a processor 118 including a user interface. The user interface may allow a user to select desired system parameters, observe results (e.g., alarms, compound IDs), or conduct any other function to operate the system or device. In some embodiments, the user interface queries the user to select a database.

The mass spectroscopy system 100 includes an ion trap 114. Ion trap mass spectrometry is an instrumental analytical method for detection and analysis of chemical substances able to detect very low concentrations of chemicals based upon the differential migration of ions through homogeneous electric field. An ion trap may include a combination of electric or magnetic fields that capture ions in a region of a vacuum system or tube. In implementations, the ion trap 114 may be part of a larger mass spectrometer system. The ions may be subsequently measured using a detector 116. Additionally, the mass spectroscopy system 100 may include an ion trap 114 and mass spectrometer capable of tandem mass spectrometry (MS/MS, $MS^2$, or $MS^n$), which may include multiple steps of mass spectrometry selection with some form of fragmentation occurring in between the stages. In some implementations, MS/MS may include tandem mass spectrometry in time and tandem mass spectrometry in space. Tandem mass spectrometry in space involves the physical separation of the instrument components (e.g., QqQ or QTOF), while tandem mass spectrometry in time involves the use of an ion trap.

In implementations, a variety of analytical devices can make use of the structures, techniques, approaches, and so on described herein. Thus, although mass spectroscopy systems 100 are described herein, a variety of analytical instruments may make use of the described techniques, approaches, structures, and so on. These devices may be configured with limited functionality (e.g., thin devices) or with robust functionality (e.g., thick devices). Thus, a device's functionality may relate to the device's software or hardware resources, e.g., processing power, memory (e.g., data storage capability), analytical ability, and so on.

Example Processes

Figure 2:
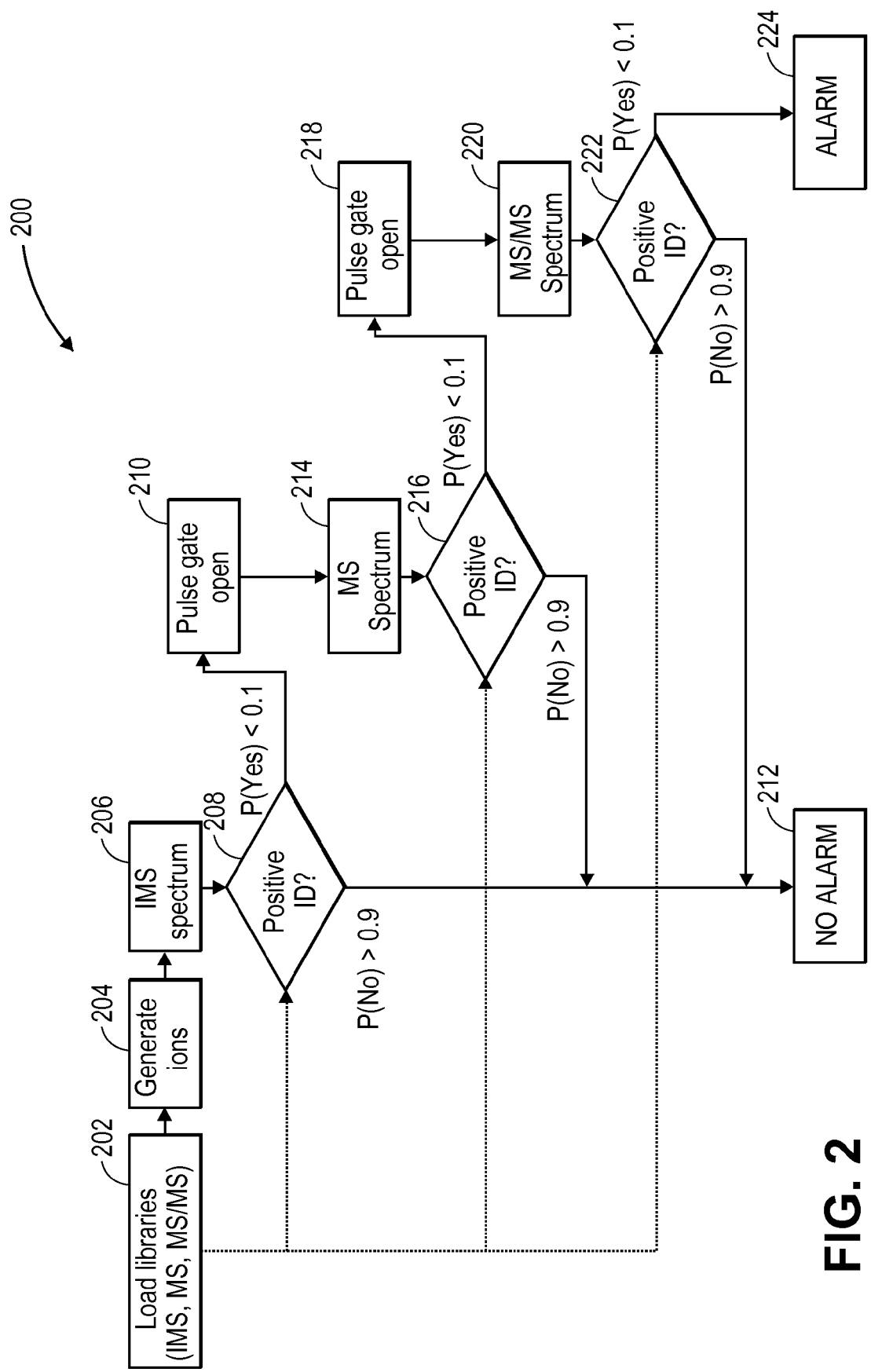
FIG. 2 is a flow diagram illustrating a method for sample introduction using, for example, the sample analysis system illustrated in FIG. 1, in accordance with example implementations of the present disclosure.

The following discussion describes example techniques for pre-screening an analyte prior to mass spectrometry analysis. FIG. 2 depicts a process 200, in an example implementation, for trace detection of an analyte using a pre-mass spectrometry screening apparatus and mass spectrometer, such as the example mass spectroscopy system 100 illustrated in FIG. 1 described above.

A library of data regarding ions and compounds is loaded by a processor (Block 202). The library 126 may include a database of spectra and/or a variety of information types about particular ions and or compounds. For example, the library 126 may include information regarding IMS, MS, and/or MS/MS spectra. In some embodiments, the processor loads the appropriate libraries and sets the operational parameters accordingly (e.g., algorithm used, event timing, etc.) upon selecting a database.

Next, ions are generated from a sample (Block 204). The ion source 102 illustrated in FIG. 1 generates ions from the sample of interest. In implementations, an ion source 102 configured to utilize atmospheric-pressure chemical ionization is used to heat the sample material, which creates a vapor. In this implementation, the resulting vapor may be introduced into drift tube 106. Other methods may be utilized for generating ions from a sample including using corona discharge, electrospray ionization (ESI), atmospheric pressure photo-ionization (APPI), and/or a radioactive source.

An IMS spectrum is created from an ionized sample (Block 206). For example, a package of ions is directed into the drift tube 106 illustrated in FIG. 1 by briefly opening a gate 104 (e.g., a Bradbury-Nielsen shutter). A portion of the ions may hit a detector 108 (e.g., Faraday cup). Subsequently, processor 118 may generate an IMS spectrum by measuring the ions that hit the detector 108. The remaining portion of the ions may pass the detector 108 (e.g., Faraday cup) and move in the direction of the ion trap 114 but may be stopped by a second, closed gate 112 that is placed between the drift tube 110 and ion trap 114.

The IMS spectrum is analyzed and compared to an analyte database (Block 208). For example, processor 118 and/or comparator algorithm 124 may compare and/or correlate the IMS spectrum with other spectra in the library 126. When processor 118 and/or comparator algorithm 124 positively correlates the obtained IMS spectrum with another spectrum in the library 126, a preliminary positive identification is made. In implementations, a positive identification may be determined when the p-value is <0.1, and a negative identification may be determined when the p-value is >0.9. In the case of a negative identification, the sample analysis is terminated and the processor indicates a "no-alarm" status (Block 212). In some implementations, a majority of analyses may take no longer than a conventional IMS analysis. Since the gate 112 remains closed, the ion trap 114 is not contaminated by this sample. The amount of extra delay drift time of the sample in the drift tube 110 may be set as desired to allow the appropriate analysis to occur (i.e., where a more time-consuming algorithm and/or sample analysis is employed, a longer drift time may be used). In some embodiments, the drift time is a preset time associated with a particular algorithm or database employed. In some embodiments, a user can select/adjust the present time. Additionally, the steps including and prior to analyzing the IMS spectrum and comparing the spectrum to other spectra in the library may be considered a pre-MS screening.

When the IMS spectrum gives a positive identification, a second gate is briefly pulsed open to let ions into the ion trap (Block 210). For example, a small portion of the sample is allowed into the drift tube 110 and/or the ion trap 114 by pulsing the gate 112. In some embodiments, the gate 112 is briefly opened when a drift time (which may be different than other drift times) corresponding to a lookup table is detected. The ions with this particular drift time now enter the ion trap 114. A second drift tube 110 may be placed between the detector 108 and the gate 112 to create sufficient time for the spectrum analysis to take place.

The ions entering the trap are used to create an MS spectrum (Block 214). The MS spectrum may be compared to another spectrum in the library 126. A positive identification of the analyte is obtained (Block 216) using the procedure discussed previously. If a second positive identification is made, the gate 112 pulses open (Block 218) and lets another portion of the sample (e.g., package of ions) into the trap to create an MS/MS spectrum (Block 220) that is compared to known spectra in the library 126. A corresponding ion mass is read from the lookup table in library 126, although other techniques can be implemented, and used to operate the ion trap 114 such that only ions within a narrow mass range are trapped. This reduces trap contamination further, and results in mass spectra with little chemical noise. If a third positive identification is made (Block 222), an alarm is raised (Block 224). In this way, even if each individual step has a relatively high false alarm rate (FAR) of 10%, the overall FAR will be only 0.1%.

The second step, creation of an MS scan, can be skipped without loss of selectivity. If the parent ion mass does not correspond to the parent mass in the lookup table, the ions are ejected during isolation and no mass spectrum is recorded in the following MS/MS scan. This leads to a correct negative ID. If the parent ion has the expected mass, it is trapped so that it can be fragmented. The fragment ion spectrum is recorded and compared to the masses in a lookup table in the library 126. This way, a positive ID only results for a correct drift time (size and shape), precursor ion mass and fragment ion masses, leading to extremely high selectivity.

There is no restriction on mechanism of gating or sample processing. Any suitable mechanism that achieves the above criteria may be employed. In some embodiments, a valve is positioned between the detector 108 and the ion trap 114 which blocks all, substantially all, or a desired portion of the sample (i.e., the gasses). Additionally, pumps or vacuums or any other desired mechanism may be used to manage the sample (see, e.g., Emary et al., J. Am. Soc. Mass Spectrom., 1:308 (1990); pulsed gas introduction into an ion trap), which is incorporated herein by reference.

Figure 3:
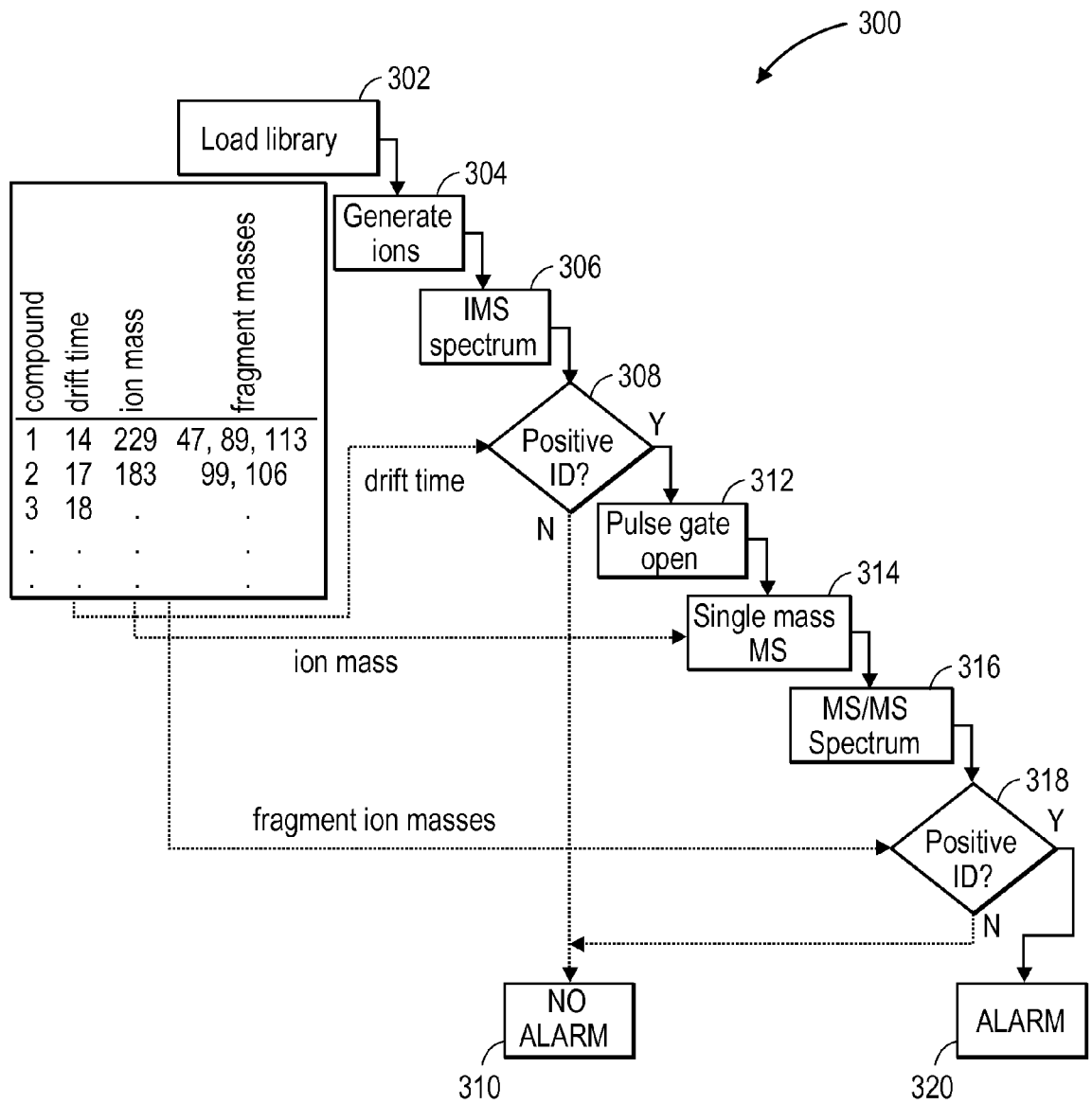
FIG. 3 is a flow diagram illustrating a method for sample introduction using, for example, the sample analysis system illustrated in FIG. 1, in accordance with example implementations of the present disclosure.

Not all steps may be needed in all cases. An exemplary overview of the decision tree, where IMS is used in the pre-screen, is shown in FIG. 3. For example, the MS spectrum generation step (Block 214) may be skipped if the connection between IMS drift time and parent ion mass of an ion of interest is known with sufficient confidence. In this case and subsequent to pulsing the gate open (Blocks 210, 312) after obtaining an IMS spectrum (Blocks 206, 306) and IMS drift time, a single mass MS spectrum (Block 314) and/or MS/MS spectrum (Block 316) may be obtained. Subsequent positive or negative identification (Block 318) may be obtained similar to the procedure discussed above. In an implementation, if a negative ID is obtained from the MS/MS spectrum (Block 316), a correlation based on a precursor ion with the expected ion mass or an expected precursor ion fragmentation may indicate a positive ID. Such decisions may be managed by the processor 118 using memory 120 and a suitable algorithm (e.g., comparator algorithm 124), where the parameters may be selected by a pre-set program and/or by a user.

Figure 4:
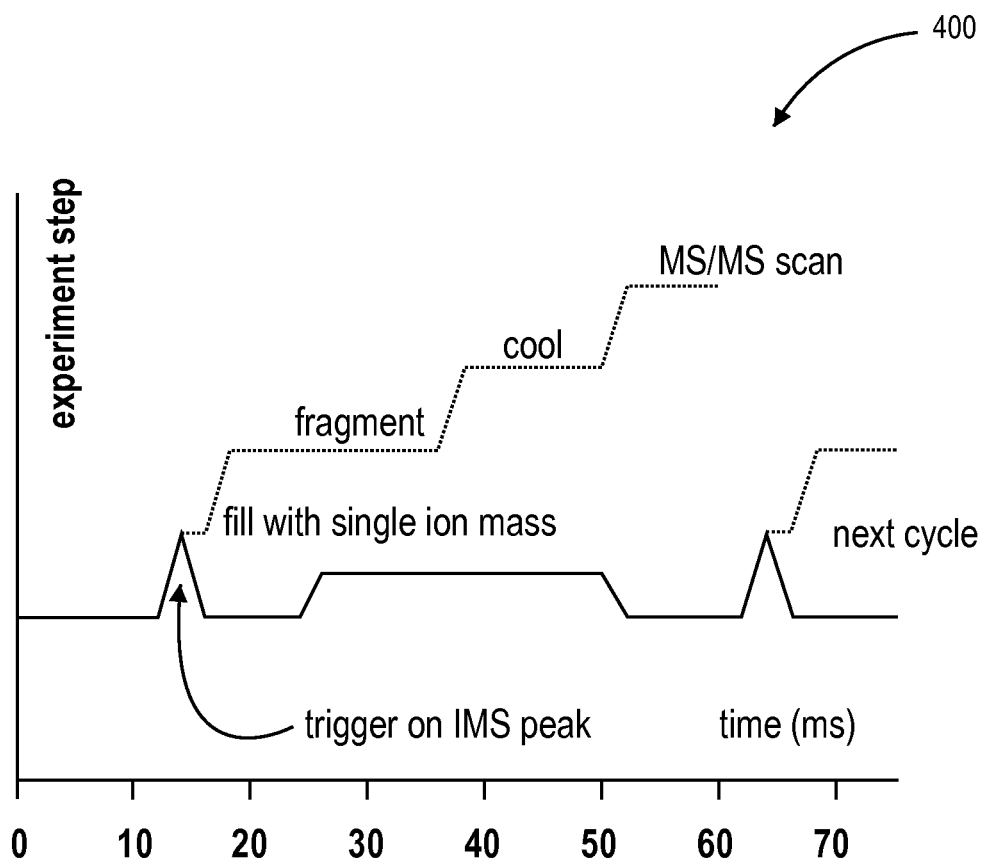
FIG. 4 is a graphical illustration of sample analysis timing in accordance with an example implementation of the present disclosure.

In some embodiments, high sensitivity is achieved by recording IMS spectra and MS spectra simultaneously. The IMS/MS timing diagram 400 shown in FIG. 4 illustrates an example of simultaneous recording. In some implementations, an IMS scan may take about 25 ms while the ion trap MS/MS duty cycle may take about 50 ms. In an implementation, two scans (e.g., an IMS scan and an MS/MS scan) may be available to use in deciding a positive identification of an analyte and whether to initiate the ion trap 114. If the IMS peak trigger time changes from one scan to the next, the ion trap process may not be finished, and there may be a need to wait one IMS scan. In this implementation, there may be no restriction on the timing of the events (e.g., recording of signal, gating, etc.). The illustration shown in FIG. 4 assumes that a positive identification can be made based on a single positive MS/MS result. In some embodiments, one may use the obtained dataset as a whole or substantially whole to make a final identification after the scan and analysis is finished. In some implementations, the mass spectrometry system 100 may have the ability to switch polarity. In some implementations, there is a potential that more than one IMS peak corresponds to a drift time in a lookup table. In these implementations, the ion trap may be set so that ions within several separate narrow mass ranges are trapped (e.g., by using stored wavefrom inverse fourier transform (SWIFT) methods).

Such systems, devices, and methods provide improved efficiency. Ion traps using $MS^n$ may identify multiple compounds in a mixture by comparing them to a large library and/or database. However, the process may often be too slow in many applications (100 library compounds@1 sec/analysis>>10 sec/sample). In systems, devices, and methods provided herein, the trap may only be used in the minority of cases (i.e., when there is a positive ID in the pre-screen (e.g., IMS spectrum)). This may reduce the average analysis time to an acceptable level even when the MS and MS/MS spectra take some time to generate. Note that throughput is defined as samples per hour, meaning that it is acceptable to spend more time on a small fraction of samples.

As illustrated with an IMS, the mass spectrometry system 100 (e.g., IMS-trap instrument) may require times for analysis as shown in Table 1 below. The times indicated in Table 1 are examples, and do not necessarily represent an optimum embodiment. For example, a complete IMS+MS+MS/MS sequence may take approximately 15 seconds (e.g., 5 seconds per scan or 5+5+5=15 seconds). However, a majority of the time the analysis can be broken off before MS/MS stage is needed so that the average time spent on a full sequence may be only 0.1*(5+0.1*(5+0.9*5)=0.88 seconds. In the example below, the average analysis time only goes from 5 seconds for an IMS-only instrument to 6.9 seconds for an instrument that performs a full IMS-MS/MS sequence when needed.

The mass spectrometry system 100 and methods herein can be embodied in a variety of forms. In some embodiments, the system may be configured to be small (e.g., desk top sized) and light weight (e.g., less than 20 kg, etc.). In some embodiments, the systems, devices, and methods herein may be configured to scan against a library of over one hundred (100+) compounds with a false alarm rate of, for example, less than 5%. In some embodiments, detections of analytes in a sample are made in less than 15 seconds (e.g., less than 10 seconds, etc.) when compared against a 100+ compound library. In some embodiments, 2 or more analytes are each detected in less than 15 seconds. In some embodiments, the systems, devices, and methods may be configured to scan against a library of 100+ compounds at a throughput rate, for example, of greater than 50 samples/hour.

The database of spectra can provide any of a variety of information types about particular ions and or compounds. In some embodiments, the database provides a look-up table that lists the compounds and corresponding drift times, ion masses, and fragments of ion masses (see FIG. 3). The database and/or library may be partitioned into one or more sub-databases, with each sub-database comprising compounds or ions of a particular type or nature (e.g., a first sub-database with ions corresponding to bioterror compounds and ions; a second sub-database with ions corresponding to environmental toxin compounds and ions; etc.). In an example, a user may select one or more databases to use according to the needs of the user and/or depending on knowledge of the sample to be analyzed.

TABLE 1

| IMS ID | P-value | Time (s) | MS ID | P-value | Time (s) | MS/MS ID | P-value | Time (s) | Weighted time (s) |
|---|---|---|---|---|---|---|---|---|---|
| negative | 0.9 | 5 | | | | | | | 4.5 |
| Positive | 0.1 | 5 | negative | 0.9 | 5 | | | | 0.8 |
| | | | positive | 0.1 | 5 | negative | 0.9 | 5 | 0.88 |
| | | | | | | positive | 0.1 | 5 | 0.72 |
| Total | | | | | | | | | 6.90 |

Ion traps tend to contaminate rapidly. The frequency and time required for cleaning and maintenance may be unacceptable for some uses (e.g., airport screening or when there is a large number of samples). It may be reasonable to assume that contamination is proportional to the amount of material brought into the trap over time. If the ion stream is deflected from the trap when no identification is needed so that only ions identified by a positive IMS peak reach the trap, a very small fraction of the material will reach the ion trap 114. In the example below (Table 2), only 1.3% of dirt reaching the detector 108 (e.g., Faraday cup) in the IMS reaches the ion trap 114.

TABLE 2

| IMS ID | P | Dirt (au) | MS ID | P | Dirt (au) | MS/MS ID | P | Dirt (au) | Dirt into trap (au) |
|---|---|---|---|---|---|---|---|---|---|
| negative | 0.9 | 1 | | | | | | | 0 |
| positive | 0.1 | 1 | negative | 0.6 | 0.05 | | | | 0.003 |
| | | | positive | 0.1 | 0.05 | negative | 0.9 | 0.05 | 0.009 |
| | | | | | | positive | 0.1 | 0.05 | 0.001 |
| Total | | | | | | | | | 0.013 |

In some embodiments, the mass spectrometry system 100 and methods comprise a computing component with a user interface. The user interface may allow the user to select desired system parameters, observe results (e.g., alarms, compound identification), or conduct any other function to operate the mass spectrometry system 100. In an example, the user interface queries the user to select a database. In implementations, a database may be selected and the processor may load the appropriate libraries and may set the operational parameters accordingly (e.g., algorithm used, event timing, etc.).

As used herein the terms "processor," "digital signal processor," "DSP," "central processing unit" or "CPU" are used interchangeably and refer to a device that is able to read a program (e.g., algorithm embodied in software) and perform a set of steps according to the program.

As used herein, the term "algorithm" refers to a procedure devised to perform a function.

As used herein, the terms "computer memory" and "computer memory device" refer to any storage media readable by a computer processor. Examples of computer memory include, but are not limited to; RAM, ROM, computer chips, digital video disc (DVDs), compact discs (CDs), hard disk drives (HDD), flash memory, and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, and magnetic tape.

What is claimed is:

1. A method of screening a sample for one or more analytes by mass spectrometry comprising:
   generating ions from the sample to create an ionized sample;
   performing a pre-mass spectrometry screening of the ionized sample;
   causing a processing system to compare results of the pre-mass spectrometry screening to an analyte database stored in a memory, wherein correlation of the result of the pre-mass spectrometry screening to an analyte within the database comprises a preliminary positive identification;
   causing a gate to open when the processing system determines that a preliminary positive identification is made, wherein opening of the gate allows a portion of the ionized sample to pass through to an ion trap of a mass spectrometer; and
   causing the gate to remain closed when the processing system determines that a preliminary positive identification is not made, wherein causing the gate to remain closed prevents the ionized sample from passing through to the ion trap of the mass spectrometer.

2. The method as recited in claim 1, further comprising:
   obtaining a mass spectrum for the portion of the ionized sample; and
   causing the processing system to compare the mass spectrum to the analyte database, wherein correlation of the mass spectrum to an analyte within the database comprises a positive identification of presence of the analyte within the sample.

3. The method as recited in claim 2, further comprising:
   causing the gate to open when the processing system determines that a positive identification is made, wherein opening the gate allows a second portion of the ionized sample to pass through to the mass spectrometer;
   obtaining a mass spectrum for the second portion of the ionized sample;
   generating an MS/MS spectrum; and
   causing the processing system to compare the MS/MS spectrum to the analyte database, wherein correlation of the MS/MS spectrum with an analyte in the analyte database confirms the positive identification of the presence of the analyte within the sample.

4. The method as recited in claim 1, further comprising:
   using the results of the pre-mass spectrometry screening to select a parent ion mass to be isolated;
   obtaining one or more mass spectrums for the portion of the ionized sample;
   generating an MS/MS spectrum for the parent ion mass to be isolated; and
   causing the processing system to compare the MS/MS spectrum to the analyte database, wherein correlation of the MS/MS spectrum with an analyte in the analyte database confirms the positive identification of the presence of the analyte within the sample.

5. The method as recited in claim 4, wherein the pre-mass spectrometry screening separates the sample into different fractions.

6. The method as recited in claim 5, wherein a fraction to an analyte within the database is passed through the gate to the ion trap.

7. The method as recited in claim 1, wherein the results of the pre-mass spectrometry screening comprise a peak, and wherein the processing system causes the gate to remain open for a period corresponding to the time that the peak occurs.

8. The method as recited in claim 1, wherein the pre-mass spectrometry screening comprises one or more of: Ion Mobility Spectroscopy (IMS), Gas Chromatography (GC), Differential Mobility Analysis (DMA), Differential Mobility Spectrometry (DMS), Field Asymmetric IMS (FAIMS), or Travelling Wave IMS (TWIMS).

9. A mass spectrometer system configured to analyze a sample for one or more analytes, the mass spectrometer system comprising:
   a pre-mass spectrometry screening apparatus configured generate ions from the sample to create an ionized sample and to pre-screen the ionized sample to generate output correlated to the composition of the sample;
   a mass spectrometer configured to receive at least a portion of the ionized sample and generate a mass spectrum of the sample;
   a sample gate configured to be opened to allow flow of at least a portion of the ionized sample from the pre-mass spectrometry apparatus to the mass spectrometer and to be closed to prevent flow of the ionized sample from the pre-mass spectrometry screening apparatus to the mass spectrometer; and
   a processing system, the processing system operable to:
   compare results of the pre-mass spectrometry screening to an analyte database, wherein correlation of the result of the pre-mass spectrometry screening to an analyte within the analyte database comprises a preliminary positive identification;
   cause the sample gate to open for a period of time upon determining that a preliminary positive identification is made; and
   cause the sample gate to remain closed upon determining that a preliminary positive identification is not made.

10. The mass spectrometer system as recited in claim 9, wherein the processing system is further operable to:
    cause the mass spectrometer to obtain a mass spectrum for the portion of the ionized sample; and
    compare the mass spectrum to the analyte database, wherein correlation of the mass spectrum to an analyte within the database comprises a positive identification of presence of the analyte within the sample.

11. The mass spectrometer system as recited in claim 10, wherein the processing system is further operable to:
    cause the sample gate to open upon determining that a positive identification is made, wherein opening the sample gate allows a second portion of the ionized sample to pass through to the ion trap;
    obtain a mass spectrum for the second portion of the ionized sample;
    generate an MS/MS spectrum; and
    compare the MS/MS spectrum to the analyte database, wherein correlation of the MS/MS spectrum with an analyte in the analyte database confirms the positive identification of the presence of the analyte within the sample.

12. The mass spectrometer system as recited in claim 9, wherein the processing system is further operable to:
    use the results of the pre-mass spectrometry screening to select a parent ion mass to be isolated;
    cause the mass spectrometer to obtain one or more mass spectrums for the portion of the ionized sample;
    generate an MS/MS spectrum for the parent ion mass to be isolated; and
    compare the MS/MS spectrum to the analyte database, wherein correlation of the MS/MS spectrum with an analyte in the analyte database confirms the positive identification of the presence of the analyte within the sample.

13. The mass spectrometer system as recited in claim 12, wherein the pre-mass spectrometry screening apparatus is configured to separate the sample into different fractions, and wherein a fraction to an analyte within the database is passed through the sample gate to the ion trap.

14. The mass spectrometer system as recited in claim 9, wherein the results of the pre-mass spectrometry screening comprise a peak, and wherein the processing system causes the sample gate to remain open for a period corresponding to the time that the peak occurs.

15. The mass spectrometer system as recited in claim 9, wherein the pre-mass spectrometry screening comprises one or more of an Ion Mobility Spectrometer (IMS), a Gas Chromatograph (GC), a Differential Mobility Analysis (DMA) apparatus, a Differential Mobility Spectrometer (DMS), a Field Asymmetric IMS (FAIMS), or a Travelling Wave IMS (TWIMS).

16. The mass spectrometer system as recited in claim 9, wherein the mass spectrometer comprises at least one of: a time of flight mass spectrometer, a single quadrupole mass spectrometer, a triple quadrupole mass spectrometer, or a magnetic sector mass spectrometer.

17. The mass spectrometer system as recited in claim 9, wherein the ion trap comprises a 3D (Paul) ion trap, a linear ion trap, a cylindrical ion trap, a toroidal ion trap, or a rectilinear ion trap.

18. The mass spectrometer system as recited in claim 9, wherein the sample gate comprises an ion gate.

19. The mass spectrometer system as recited in claim 17, wherein the ion gate comprises a Bradbury-Nielsen shutter.

20. The mass spectrometer system as recited in claim 9, wherein the sample gate comprises a fast pneumatic valve.

21. A method of screening a sample for one or more analytes by mass spectrometry comprising:
   generating ions from the sample to create an ionized sample;
   performing an Ion Mobility Spectrometry (IMS) screening of the ionized sample;
   causing a processing system to compare results of the Ion Mobility Spectrometry (IMS) screening to an analyte database stored in a memory, wherein correlation of the result of Ion Mobility Spectrometry (IMS) screening to an analyte within the database comprises a preliminary positive identification;
   causing a gate to open when the processing system determines that a preliminary positive identification is made, wherein opening of the gate allows a portion of the ionized sample to pass through to an ion trap of a mass spectrometer; and
   causing the gate to remain closed when the processing system determines that a preliminary positive identification is not made, wherein causing the gate to remain closed prevents the ionized sample from passing through to the ion trap of the mass spectrometer.

* * * * *